United States Patent [19]

Pollak et al.

[11] Patent Number: 4,954,714
[45] Date of Patent: Sep. 4, 1990

[54] APPARATUS FOR TIME-RESOLVED PHOTOGRAPHY OF FLUORESCENCE

[75] Inventors: Alfred Pollak; Michael Maszkiewicz, both of Toronto, Canada

[73] Assignee: HSC Research Development Corporation, Toronto, Canada

[21] Appl. No.: 248,723

[22] Filed: Sep. 26, 1988

[51] Int. Cl.[5] ................. G03B 15/04; G03B 42/08; G03C 5/04
[52] U.S. Cl. .................. 250/458.1; 250/459.1; 378/45
[58] Field of Search ............. 250/350, 351, 458.1, 250/459.1, 461.1; 378/44, 45

[56] References Cited

U.S. PATENT DOCUMENTS

| | | | |
|---|---|---|---|
| 4,058,732 | 11/1977 | Wieder | 250/461.1 |
| 4,101,221 | 7/1978 | Schunck et al. | 250/351 X |
| 4,105,333 | 8/1978 | Kaule et al. | 250/459.1 |
| 4,198,567 | 4/1980 | Eneroth | 250/459.1 |
| 4,336,459 | 6/1982 | Fay | 250/459.1 |
| 4,542,290 | 9/1985 | Tan et al. | 250/213 VT |
| 4,612,660 | 9/1986 | Huang | 378/44 |

OTHER PUBLICATIONS

"Two Chopper Technique for Measuring Fluorescence Lifetimes", K. A. Ingersoll, Applied Optics, vol. 15, No. 1, Jan. 76.

Primary Examiner—Constantine Hannaher
Assistant Examiner—J. Eisenberg
Attorney, Agent, or Firm—Banner, Birch, McKie & Beckett

[57] ABSTRACT

A time-resolved photographic analysis device is capable of analyzing for the presence of fluorescent radiation, particularly in a diagnostic sample. The apparatus comprises a light source for emitting exciting pulses as directed onto the sample. A camera is provided which is focused on the sample with the camera continually exposed to the sample. A chopper device is used in conjunction with the camera to prevent exposure of the photographic film in the camera to background fluorescence generated by miscellaneous components in the sample. Fluorescent labels, if present in the sample, are designed to fluoresce over considerably longer periods than the background fluorescence. A device is provided to coordinate the operation of the chopper device with the rate of flashing of the light source to ensure that the photographic film is only exposed to fluorescent radiation which would be generated by a fluorescent label in the sample being analyzed.

12 Claims, 5 Drawing Sheets

APPARATUS FOR TIME-RESOLVED PHOTOGRAPHY OF FLUORESCENCE

FIELD OF THE INVENTION

This invention relates to the time-resolved photographic analysis of emitted fluorescence from an excited sample.

BACKGROUND OF THE INVENTION

Most materials when exposed to high intensity radiation, particularly in the UV range, will naturally fluoresce for a period of time after the pulse of exciting radiation has subsided. Sometimes it is desirable, however, to record fluorescence of a fluorescent label present in a sample to be analyzed, where fluorescent radiation from the label must be distinguished from background fluorescent radiation emitted by other excited components in the sample. One technique in distinguishing background fluorescence from that of the fluorescing label is to make the label from a material which has a considerably longer fluorescing lifetime than the normal short life of background fluorescence. By conducting a time-resolved analysis of the fluorescence from the activated sample, the background fluorescence can be eliminated by allowing it to subside before analyzing for any fluorescent radiation from the label, if present in the sample.

This technique of analysis is very useful in a variety of diagnostic testing procedures. For example, the fluorescent label may be linked to a molecule which has an affinity for the molecule to be detected in the sample. An example of this technique is the common immunoassay. Time-resolved analysis of the fluorescent radiation is usually accomplished by a gating device, which is normally of electronic construction. Examples of such electronic gating devices are disclosed in U.S. Pat. Nos. 4,058,732; 4,198,567; and 4,612,660. Each of these patents discloses an electronic type of gating circuit which permits analysis of the fluorescent radiation after a predetermined delay from the time the sample was excited with a pulse of radiation directed on the sample.

Another form of gating system is disclosed in U.S. Pat. No. 4,336,459. This system is used to detect in daylight the presence of certain minerals in an uncovered ground sample. The gating may be accomplished by either an electronic actuated optic shutter or the shutter on a camera. One of the difficulties associated with this system is that the gated camera shutter cannot be opened and closed at sufficient speed to be applied in detecting fluorescence from a small concentration of fluorophores having shorter lifetimes of fluorescence.

In the fields of immunoassaying and DNA detection, there is significant demand for the ability to analyze for trace amounts of fluorescence. As is appreciated, fluorometry is a viable method in medical diagnostics, because it avoids the generally accepted hazardous radiation counting techniques. Background fluorescence continues to be one of the most significant problem in conducting such analysis. Background fluorescence can mask the radiation from the label and thereby confuse the test. Background fluorescence is emitted by many biological substances, such as blood serum, as well as solvents, plastics, glasses, papers and the like. These materials are commonly present in the medium or support for the sample to be analyzed. Another problem with fluorometry is the background interference caused by scattered radiation emitted by the excitation source. This also must be eliminated to improve accuracy of the test.

It has become possible to use fluorophores or labels which have a lifetime significantly longer than that of the background emissions from other components in the sample. Fluorescent rare earth chelates have lifetimes in the range of tens to thousands of microseconds, whereas the lifetime of the background fluorescence is normally in the range of tens to no more than hundreds of microseconds. The typical gated fluorometer of the type disclosed in the above patents, measures the intensity of the fluorescence starting after a predetermined delay time following the excitation pulse. This time-resolved approach allows the unwanted background emissions to subside to an insignificant level.

In medical diagnostics based on DNA fluorescent probing the testing is mostly qualitative. For this purpose time-resolved recording of the fluorescent image on a photographic film is sufficient.

Technically the problem is reduced to the question of how to photograph the fluorescence which is still being emitted after a specific time delay, usually hundreds of microseconds long, with respect to the excitation pulse. In other words, the opening of the shutter must occur after the given delay, and then the shutter has to open very rapidly that is, the process of its opening has to be not much longer than few hundreds of microseconds.

While the exposure time in modern conventional cameras can be as short as 250 μs, the actual process of opening the shutter is much slower. This is because the very short exposures are accomplished by relatively slow movement, across the film surface, two curtains one following the other with a time delay equal to the exposure time. This means that, for example, for an exposure of 250 μs, only a narrow slit of about 1 mm wide is travelling across the film. In effect the image of the object is recorded in strip by strip manner and if during the time of the slit sweep the object changes the intensity and wavelength composition of its emission, the photographic image will be recorded as changing its intensity and color also, along the direction of the slit movement. In conventional cameras it takes normally at least 10 milliseconds to complete one full sweep, which is definitely far too long if the recorded fluorescence has a lifetime of 1 ms. In such a case almost all the observed change of the fluorescence would be recorded on only 1/10 of the film frame length.

For the purpose of high speed photography streak cameras were developed. In this case, a very narrow slit placed in the optical path is swept across the film surface but at very high speed, comparable to the speed of the recorded event. As the event grows along the slit, it is recorded in graphical form with time in the one direction and position in the other.

The other photographic method used for recording fast changing events is high speed framing in which a series of pictures is taken covering the event. This is equivalent to the concept of a high speed motion picture camera.

There exist also the class of high speed camera shutters which are entirely non-mechanical. These include magneto- and electro-optical shutters, image intensifying tubes and electronic streak and framing cameras.

SUMMARY OF THE INVENTION

According to an aspect of the invention an apparatus for time-resolved photographic analysis of an excited sample capable of emitting fluorescent radiation comprise radiation emitting means for radiation pulses at a prescribed frequency for exciting a sample which may contain a label capable of fluorescing on a prolonged basis when excited, compared to short-life background fluorescence of the sample. Holding means holds a sample to be analyzed, while focusing means focuses radiation pulses emitted by the radiation emitting means along a first path towards a sample held by the holding means. A camera is focused along a second path on a sample held by the holding means where the second path diverges in relation to the first path. The camera is adapted to expose continuously a photographic film in the camera at least while the apparatus is in operation. A rotating chopper element is provided which has at least one aperture located therein for repetitiously crossing the second path. Drive means is provided for rotating the chopper element. Coordinating means coordinates the phase relationship of the rotation of the chopper element relative to the prescribed frequency of pulses from the emitting means. The coordinating means is adjustable to select a phase relationship which causes each of the apertures to cross the second path to expose photographic film of the camera to fluorescent radiation emitted by a fluorescing label present in a sample after short-life background fluorescence of sample components has subsided and before the next pulse of radiation from the emitting means occurs. Photographic film in the camera is repetitively exposed to fluorescence radiation to record thereby all photon energy from repetitive exposures on said photographic film of fluorescence radiation received from repetitive fluorescent emissions of a fluorescing label in a sample being analyzed.

BRIEF DESCRIPTION OF THE DRAWINGS

Preferred embodiments of the invention are illustrated in the drawings, wherein.

DETAILED DESCRIPTION OF THE PREFERRED EMBODIMENTS

The apparatus of this invention provides for the time-resolved photographic recording of fluorescence radiating from a sample after the background fluorescence has subsided. The apparatus provides for such photographic recording without the need of a high speed streak or framing camera, or any other type of fully electronic imaging system. In accordance with this invention, a conventional photographic camera may be used in combination with an electromechanical chopper element which serves as the high speed shutter for the system.

Figure 1:
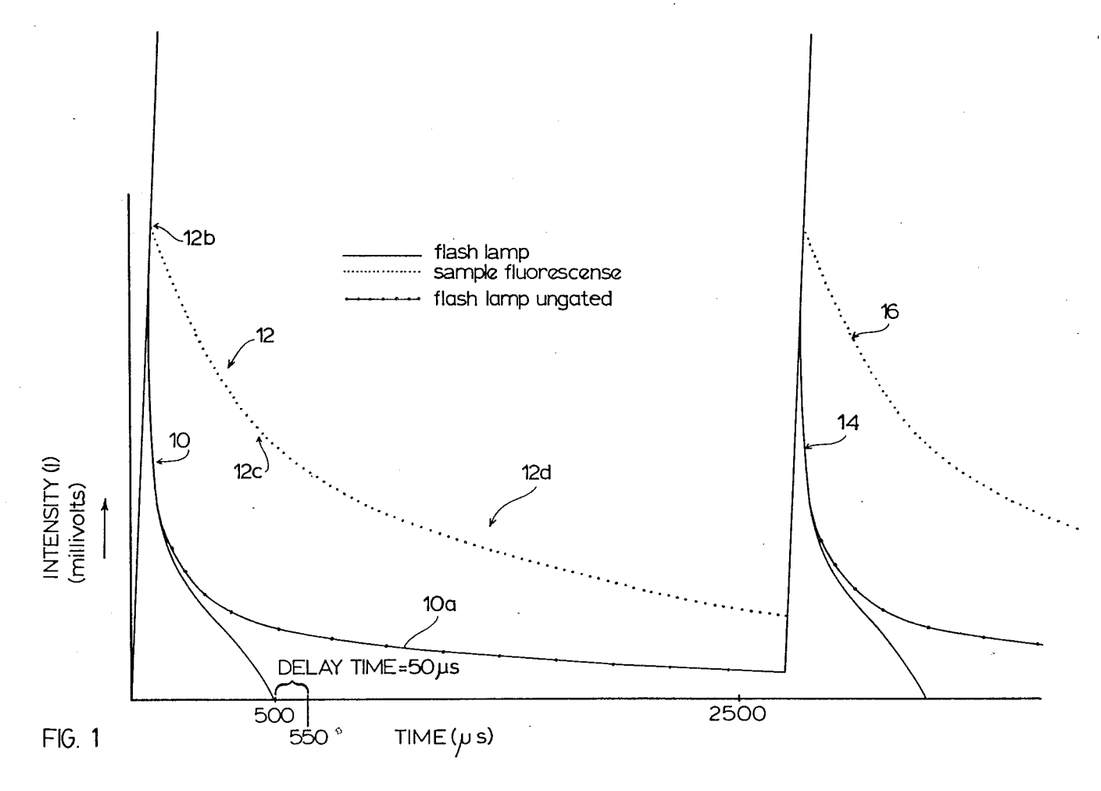
FIG. 1 is a plot of the intensity of incident radiation and fluorescent radiation over time.

In order to produce the desired effect by the fluorescent label or fluorophore used in the sample, it is necessary to provide a fluorophore which is capable of fluorescing over prolonged times compared to the background fluorescence. Most background fluorescence subsides within approximately 50 to 100 $\mu s$ after the peak of the excitation pulse of radiation from the exciting source. With reference to FIG. 1, a sample is exposed to a pulse of radiation from the xenon flashlamp which may have a half width of 10 $\mu s$. An example of the intensity over time of this type of pulsed radiation is shown as the black line 10 of FIG. 1. The output of the light source may be gated so that at approximately 500 $\mu s$ from zero time, the output of the lamp is blocked. If the lamp output is not chopped, the radiation from the lamp slowly subsides as indicated by line 10a. This is due to the typical Xenon flashlamp so called afterglow during which it continues to emit radiation of various wavelengths. It is appreciated that suitable filters may be used to block out this unwanted trail of radiation from the lamp.

The sample as exposed to the pulse of light will start to fluoresce almost immediately. The peak of the fluorescent radiation at 12b is due to the combined fluorescence of the sample components and the fluorophore which, in this instance is present in the sample. The fluorescence degrades exponentially as indicated by downwardly sloping line 12c. In the transition phase in the range 550 $\mu s$ and onwards there is little, if any, background fluorescence remaining. The fluorescence indicated by line 12d is due strictly to the longer life of the fluorophore, hence the plot of FIG. 1 indicates the presence of the fluorophore in the sample.

It is during this period that the photographic film of the camera is exposed to the sample, to record any and all photons arriving on the film from the fluorescent radiation in the period of approximately 550 to 2500 $\mu s$. That means that in the specific case of time relations, illustrated in FIG. 1, the photographic film starts to be exposed after a delay time of 50 $\mu s$ with respect to the moment of complete blocking of the flashlamp. Generally that delay time can be set to any value between zero and several hundreds of microseconds. Also the indicated values of FIG. 1 for the interval needed to block the lamp after the pulse and value of the interval between consecutive pulses are illustrative only and depend on specific technical details of the apparatus. After the desired exposure period, the camera is gated and the next pulse 14 is emitted by the exciting source to repeat the process in activating the fluorophore of the sample. Similarly, the fluorescence of the sample repeats the curve of fluorescent radiation, as indicated by line 16. Also, the output of the light source is chopped to abruptly cut off the radiation of the lamp as impinging on the sample.

Figure 2:
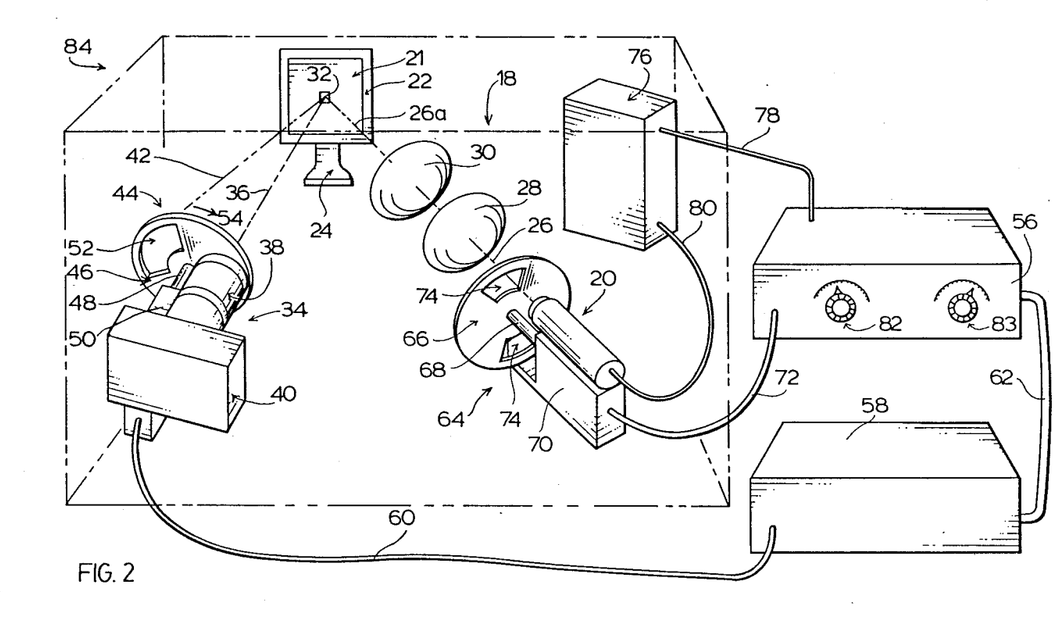
FIG. 2 is a perspective view of the apparatus according to one embodiment of the invention for the time-resolved photographic analysis of fluorescence in a sample.

An embodiment of the apparatus according to this invention for analyzing and determining the presence of a fluorophore in the sample on a time-resolved basis, is shown in FIG. 2. The apparatus generally designated 18 comprises a source 20 for emitting radiation pulses which excite the sample 21 as contained in a transparent container 22 held by a holder 24. The radiation pulses from the source 20 travel along a first path, as indicated by line 26. It is appreciated that a variety of devices are available for emitting the radiation pulses, for example the source 20 may be a flashlamp such as the Xenon flashlamp or source 20 may be a laser of the desired wavelength of emitted radiation. For the particular fluorophore chosen, the flashlamp or laser emits radiation at a suitable wavelength to induce fluorescence in the sample. For most fluorophores, suitable excitation radiation is found in the UV range. Depending upon the type of source, focusing of the radiation emitted from the source may be necessary as shown in FIG. 2. Lenses 28 and 30 are used to collimate and focus the radiation onto the sample 21 as indicated by the square region 32. The light along the portion of the path 26a is focused into a spot of approximately the same size as the sample 32.

The sample as excited by the pulse of UV radiation will fluoresce in the manner demonstrated in FIG. 1. The fluorescent radiation is emitted from the sample 32 in all directions. A camera, generally designated 34, is positioned to focus along a second path 36 as directed towards the sample 32. Hence any fluorescent radiation radiating from the sample as it travels along the second path 36, enters the lens portion, generally designated 38, of the camera 34 to focus the incoming fluorescent radiation on photographic film contained in the camera body 40. The second path 36 is along a line which diverges relative to the first path 26. To avoid any reflected light travelling along path 26 directly impinging on the camera 34, the path 36 is at an angle relative to the incident path to avoid reflected light which, in accordance with standard principles of physics, is reflected primarily along line 42.

During operation of the apparatus, the shutter of the camera 34 is held open to expose continuously the photographic film which is stationary in the camera. To control, however, the fluorescent radiation which enters the camera, a rotating chopper device 44 is provided in front of the camera lens 38.

The rotating chopper element 46 is mounted on shaft 48 which is driven by electronically controlled electric motor 50. The motor acts as the drive means for rotating the shaft 48 and hence rotating the chopper element 46 at a desired rpm which provides the necessary chopping action to expose the photographic film in the camera to the desired region of fluorescent radiation from a label in the sample if it is present. This will avoid exposing the camera to any background radiation in the sample after initial excitement thereof. The rotating chopper element has at least one aperture, generally designated 52, provided therein which repetitiously crosses the second path 36 as the chopper element is rotated in the direction of arrow 54.

A device is provided for coordinating the phase relationship of the rotation of the chopper element 46 relative to the prescribed frequency of radiation pulses from the lamp 20. According to the embodiment of the invention shown in FIG. 2, the output of the lamp 20 is also chopped to select a predetermined time portion of the radiation pulse in order to remove long lasting trailing radiation (afterglow) emitted by the Xenon flashlamp. This aspect of the invention is illustrated in FIG. 1 where, after approximately 500 μs, the output of the lamp is chopped so that the intensity at any emission thereof drops to zero. The second chopper device, generally designated 64, has a second chopper element 66 as mounted on drive shaft 68. The whole system is controlled by the controller device which, in this embodiment, consists of linked controller 56 and 58. Controller 58 controls motor 50 through signals in cable 60. Controller 56 communicates with controller 58 through cable 62. The drive shaft 68 is driven by motor 70 which is in electronic communication with its controller 56 via cable 72. For sake of convenience, the lamp 20 is mounted on top of the motor 70. The chopper element 66 has at least one aperture, and in this embodiment is provided with two apertures generally designated 74.

In accordance with the embodiment shown in FIG. 2 of this invention, the flashlamp 20 is of the Xenon type having a power pack, generally designated 76, which is controlled by a controller 56 through cable 78. On command the power pack 76 causes the lamp 20 to flash by supplying the necessary trigger pulse through line 80. The Xenon flashlamp of this invention is capable of flashing on a highly repetitive basis, with a frequency in the range of up to 400 Hz.

Controllers 56 and 58 coordinate the phase relationship between the pulses from the lamp 20 and the rotations of the choppers 44 and 46, to provide that the film of the camera is exposed to any fluorescent radiation radiating from the sample 32, after the background fluorescence has subsided. According to this embodiment, controller 58 is a slave to controller 56. Controller 56 is provided on its front face with an adjustable dial 82 which may be moved to select the desired phase relationship in setting up the operation of the apparatus and dial 83 is provided for setting the equal frequency of rotation of both chopper elements 46 and 66 and consecutively the frequency of pulsation of the lamp 20. It is appreciated, of course, that in the event that a single chopper unit 44 is used with the camera, where the correct wavelength and duration of radiation can be provided by the lamp 20 without help of the second chopper 66, only one controller 56 is needed as linked directly to the motor 50 through cable 60.

By virtue of the shutter of the camera 34 being open at all times during operation of the apparatus 18, it is important to conduct sample analysis in a dark room or to enclose the apparatus 18 within a suitable cabinet, generally designated 84, to house at least the lamp, sample, camera lens, chopper elements and lenses. Above the sample holder 24 a hatch or suitable door may be located to permit insertion and extraction of the sample 32 in the container 22. This hatch when sealed blocks out all light entering the cabinet 84. The rear of the camera box 40 is normally outside of the cabinet to facilitate replacement of film.

Figure 3A:
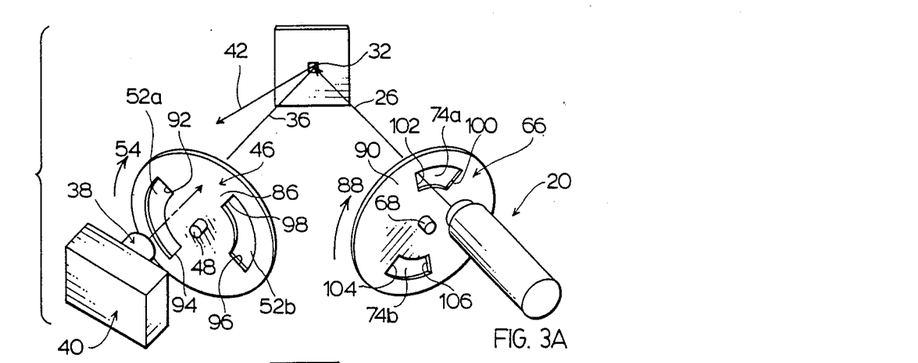
FIGS. 3a, 3b and 3c schematically show in sequence the relationship of the chopping elements to the flashlamp and the camera.

As shown in FIG. 3a, the phase relationship of rotating chopper element 66 to rotating chopper element 46 is such that aperture 74a is crossing the first path 26 while the second path is blocked by the body portion 86 of the chopper element 46. With this synchronized relationship of the chopper elements, the phase relationship of the rotation of chopper element 66 to the pulsation of flashlamp 20 may be coordinated to trigger the flashlamp 20 to emit a pulse of excitation radiation along the first path 26 before rotation of the chopper element 66 in the direction of arrow 88 causes the body portion 90 of the chopper element to block off any further radiation being emitted by the lamp source.

Chopper element 46 has diametrically opposing apertures 52a and 52b. Aperture 52a in the direction of rotation of the chopper element and a trailing edge 94. The other aperture 52b in the direction of rotation of the chopper element has a leading edge 96 and a trailing edge 98. According to this preferred embodiment, the leading and trailing edges of each aperture 52a and 52b extend in a radial direction outwardly from the axis of the shaft 48. The radial location of the apertures 52 and 52b is such that as the chopper element rotates, each aperture crosses the second path 36.

Chopper element 66 has apertures 74a and 74b which are diametrically opposed. The apertures are of similar construction as the apertures of element 46. Aperture 74a has a leading edge 100 and a trailing edge 102 in the direction of rotation 88. Aperture 74b has a leading edge 104 and a trailing edge 106. The leading and trailing edges of each aperture 74a and 74b extend in a radial direction relative to the axis of the shaft 68. The apertures 74a and 74b are radially located so as to cross path 26 as the chopper element rotates in the direction of arrow 88.

It is appreciated that both chopper elements need not be in the shape of discs, instead the elements could be propeller shaped having openings constituted by an extension of apertures 52 and 74 in the outward direction, the remaining body portion of the chopper element would then constitute a blade of the element construction. It is also appreciated that chopper elements should be provided with enclosures around its edges to avoid operator injury.

Figure 5:
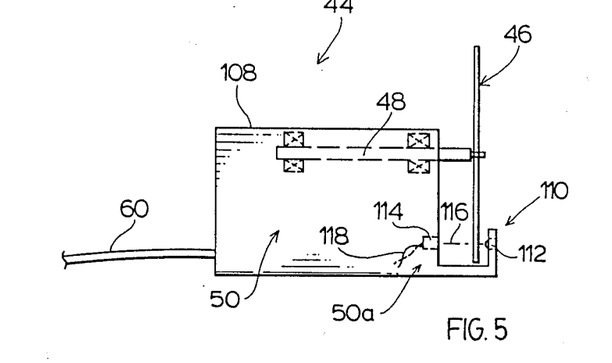
FIG. 5 is a side elevation of the chopper element of FIG. 2.

The coordinating device in the form of cooperating controllers 56 and 58, require input regarding the position of apertures 52 and 74 in chopper element 46 and 66 respectively, to coordinate the phase relationships of the timing of the lamp flash compared to the positions of the apertures in the chopper elements 46 and 66. There are a variety of techniques available to detect the position of the apertures in the chopper element, the preferred system for the case of chopper device 44, being shown in FIG. 5. The motor 50 in casing 108, drives the drive shaft 48 to which the chopper element 46 is secured. An aperture position-detecting device 110 is positioned at the base 50a of the chopper device 44. The device 110 comprises a light emitting diode (LED) 112 aligned with a photoelectric cell 114. When the respective aperture 52a and 52b of the chopper element 46 crosses the path 116, light from LED 112 reaches photoelectric cell 114 to emit a signal in line 118. The signal in line 118 is transmitted along cable 60 which in turn is coupled to slave controller 58. Exactly in the same way, the position of apertures 74a and 74b of chopper element 66 is detected and the appropriate signal is sent along cable 72 to master controller 56. In the simplified version of the described apparatus, only one chopper, that is 46, and only one controller, that is 56, can be used. The controller 56 sets then the frequency of rotation of chopper element 46 by controlling the motor 50, receives directly (as there is no controller 58) the signal from line 118 from the photoelectric cell 114 and produces the signal in cable 78 for triggering the flashlamp 20. The dial 83 on controller 56 is used to establish the proper phase relation between the position of chopper element 46 with respect to the camera lens 38 and the moment of the flash from the lamp 20. That is the UV light pulse from that lamp is fixed always when light path 36 is blocked by the body portion 86 of the chopper element. As the chopper element 46 continues to rotate, then after a certain delay time (which can be adjusted by dial 83) with respect to the moment when the leading edge of the respective aperture crosses the path 36, then photographic film in the camera 40 starts to be exposed to any fluorescent radiation being emitted by the sample well after background fluorescent radiation has subsided.

As explained with reference to FIG. 2, it is sometimes desirable to have a chopper device 64 to cut off trailing radiation emitted by the flashlamp 20 after the main pulse. A representative output of the lamp as gated is shown in FIG. 1. With reference to FIG. 3a it is preferred to trigger the flashlamp 20 just before the trailing edge 102 of aperture 74a crosses the first path 26. Once the phase relationship for triggering the pulse from lamp 20 is coordinated with the rotation of the chopper element 66, then rotation of chopper element 46 is adjusted by controller 56 via slave controller 58 to ensure that the leading edge 92 of aperture 52a crosses the second path 36 at least at 500 μs after the flash is initiated by a trigger pulse from the power supply 76, that is, when the flashlamp 20 is already completely blocked by the body portion 90 of the chopper element 66. Of course, that time of crossing the path 36 by edge 92 can be at any value between approximately 500 and 2500 μu, depending on how long delay time (see FIG. 1) is the best one for a given sample. The flash from lamp 20 as it travels along path 26 illuminates the sample 32 where incident light is reflected along path 42 away from the second path 36 so that reflected light does not impinge on the camera 40. The incident light, however, is at a wavelength and power sufficient to excite molecules in the sample 32 to cause observable fluorescence. As previously discussed in the diagnostic technique, should a fluorescent label be present in the sample it will also be excited to fluoresce. The fluorophore or label is of a substance which has a relatively long fluorescence lifetime compared to short-lived background fluorescence from other components in the sample 32.

Figure 3B:
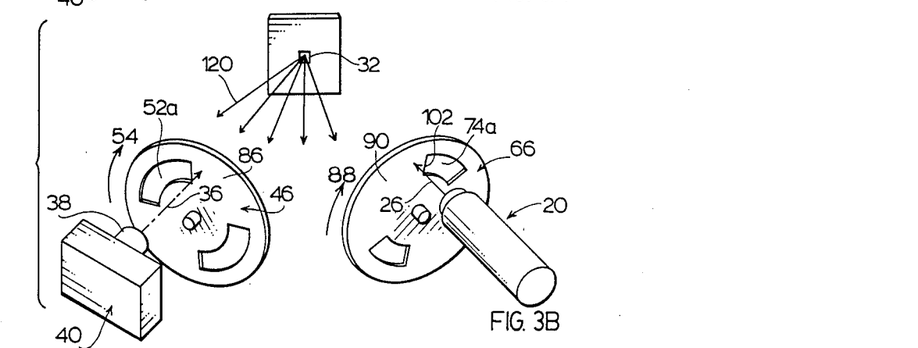

As shown in FIG. 3b, any trailing radiation from lamp 20 is chopped by the body portion 90 of the chopper element 66 by virtue of the trailing edge 102 crossing the path 26. With reference to FIG. 1, this point in time may be in the region of 500 μs from the initiation of the flash. In the meantime, sample 32 is emitting fluorescent radiation as indicated by lines 120. The lines 120 are diverging to indicate that the fluorescent radiation is being emitted in all directions. At this point in time the background fluorescence may still be a factor in the radiation 120, that is, in the region of 500 to perhaps 550 μs after the trigger pulse for the flash. The chopper element 46 is therefore in a position such that the body portion 86 continues to block radiation travelling along path 36.

Figure 3C:
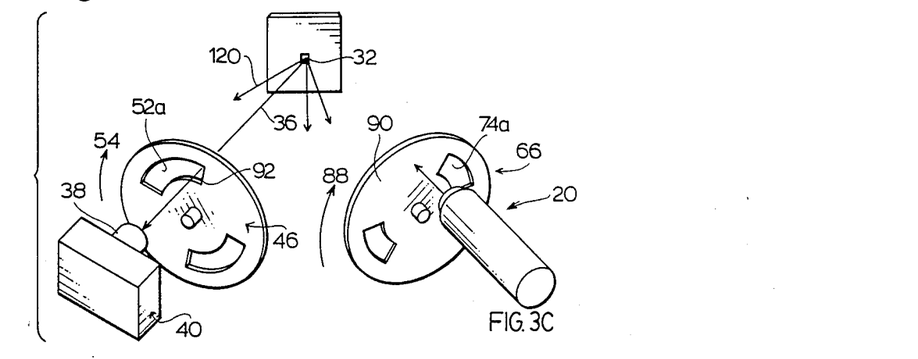

With reference to FIG. 3c, any trailing radiation from lamp 20 continues to be blocked by body portion 90 of chopper element 66. However, at this point the leading edge 92 of aperture 52a has crossed path 36, hence any photons of the radiation 120 travelling along path 36 is admitted to the camera 40 through the lens 38 to expose the photographic film in the camera. The aperture 52a extends in the circumferential direction through an arc of a sufficient number of degrees to expose the film in the camera 40 to any radiation 120 which is emitted by the sample in the region of approximately 550 μs to 2500 μs after the trigger pulse for the flash 20. As shown in FIG. 1, this phase relationship in the timing of the position for the aperture 52a allows then to expose the photographic film to the region 12d of fluorescent radiation being emitted by the sample 32. In the meantime, any trailing radiation from the lamp 20 is blocked out so that the region 10a of FIG. 1 does not occur to indicate falsely the presence of fluorescent radiation from the sample 32. There is, therefore, a sensitive balance in the size of the apertures 52 and 74, the speeds of rotation of the chopper element 46 and 66, the timing of the pulse flash from lamp 20 and the removal of any trailing radiation from the lamp 20 to determine, at least on a qualitative basis, whether or not fluorescent labels of long lasting fluorescence capabilities are present in the sample.

It is appreciated that a variety of other chopper systems may be used in conjunction with the camera, and optionally the light source to produce the desired result in exposing the camera to the selected period between lamp flashes to receive any fluorescent radiation which would be emitted by a fluorophore if present in the sample.

Figure 4:
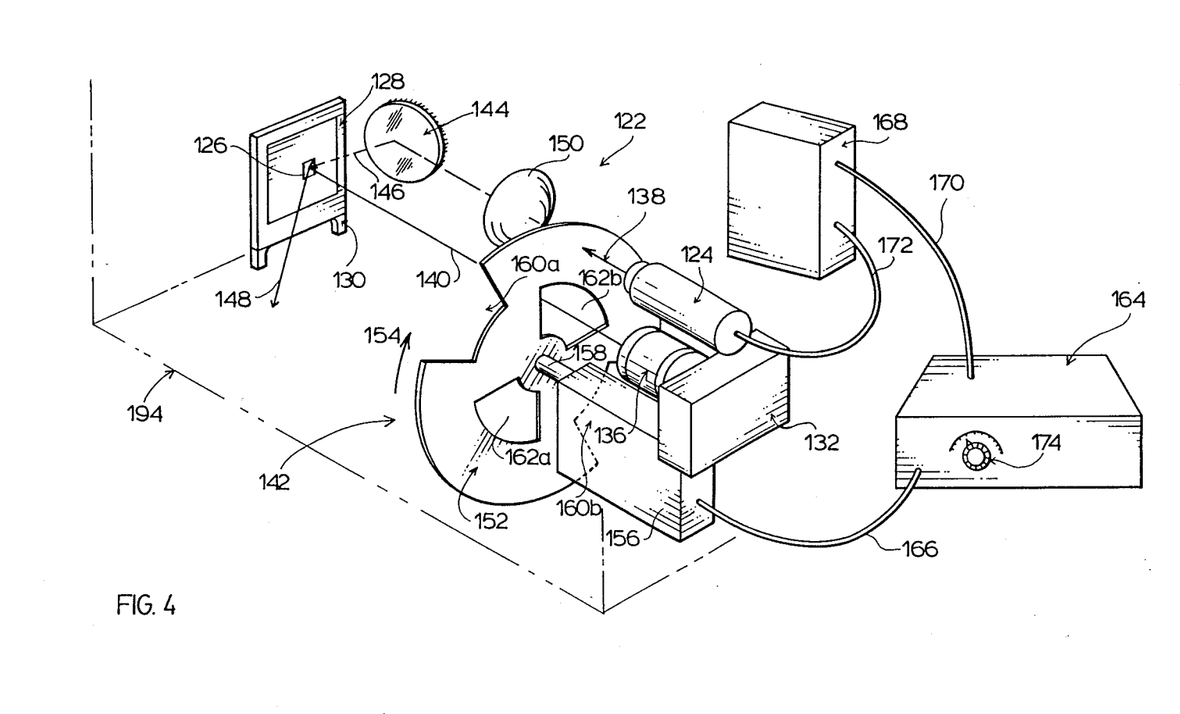
FIG. 4 is a perspective view of an alternative embodiment of the invention.

FIG. 4 shows an alternative embodiment for the chopper system. The apparatus 122 has a flashlamp 124 which may be the same as flashlamp 20 of FIG. 1. A sample 126 is provided in a sample container 128 which is held on a suitable support 130. A camera 132, which may be the same as camera 40 of FIG. 1 is provided with photographic film to record fluorescent radiation through the camera lens 136. The lamp 124 emits pulses of radiation along a first path 138, fluorescent radiation emitted by the sample 126 is directed towards the camera along a second path 140. A chopper device 142 is provided to control in the manner discussed with respect to FIGS. 3a through 3c, the exciting pulsed radiation from the lamp 124 and the fluorescent radiation which is received by the camera 132. The lamp 124 may be mounted on top of the camera 132 such that the first path 138 is essentially parallel to the second path 140. A suitable reflecting device in the form of, for example, a mirror 144 is provided in the first path 138 to reflect the incident radiation along path 146 onto the sample 126. The incident radiation 146 is reflected along path 148 away from the second path 140 so that reflected radiation will not impinge upon the camera 132. A suitable lens 150 is provided to focus the incident radiation on the sample 126 so as to illuminate most, if not all, of the sample 126.

The chopper device 142 has a rotating chopper element 152 which is rotated in the direction of arrow 154 by motor 156. The chopper element 152 is mounted on shaft 158 as rotated by the motor 156. The chopper element has two sets of apertures, the first set of apertures 160a and 160b are at a first radial location to cross the first path 138; a second set of apertures 162a and 162b are provided at a second radial location inwardly of the first. The second set of apertures 162a and 162b cross the second path 140. In this arrangement a single chopper device performs the same functions as the two chopper devices 44 and 64 of FIG. 1, under the control of a single coordinating device 164 for synchronizing the triggering of the flashlamp 124 relative to exposing the photographic film in the camera 132. The motor 156 is linked to the controller 164 by cable 166, the power pack 168 for the flashlamp is linked to the controller 164 through cable 170. The power for the flashlamp 124 and the trigger pulse is transmitted to the lamp 124 through cable 172. The chopper device 142 may be equipped with a similar aperture location device 110 of FIG. 5 to indicate the location of the leading edge of each aperture 160a and 160b. The signal indicating the leading edge crossing the path of the sensing device is transmitted through cable 166 to controller 164. Controller 164 may be programmed with a suitable delay time as determined by adjustment knob 174 to actuate the power pack 168 to transmit a trigger signal through cable 172 which in turn actuates the pulse of excitation radiation from the lamp 124.

Figure 6:
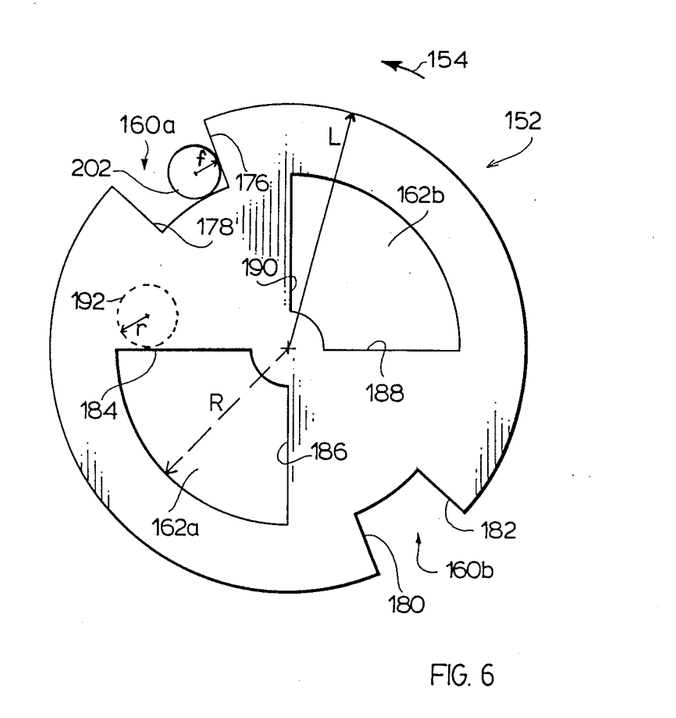
FIG. 6 is a plan view of the chopper element of FIG. 4.

FIG. 6 shows the chopper element 152 in more detail. Apertures 160a and 160b each have a leading edge 178 and a trailing edge 176 for aperture 160a, and a leading edge 182 and a trailing edge 180 for aperture 160b. Similarly, aperture 162a has a leading edge 186 and a trailing edge 184, aperture 162b has a leading edge 190 and a trailing edge 188. The aperture position detection device as employed on the chopper device 142, detects the leading edge 178 and 182 of the respective apertures 160a and 160b. Once this position is known, controller 164 then times out the delay, before the trigger pulse is transmitted from the power pack 168 to the flashlamp 124 to emit a pulse of radiation. This would be done before trailing edge 176 of aperture 160a is about to cross path 138. Depending upon the speed of rotation of the chopper element, approximately 300 μs should pass before trailing edge 176 totally blocks off the first path 138. With continued rotation of the chopper element 152 in the direction of arrow 154 the trailing edge 190 of the aperture 162a crosses path 140 and at that time the photographic film in the camera starts to be exposed to fluorescent radiation which would be in the region 12d of the fluorescent output from the sample, as shown in FIG. 1.

For purposes of coordinating the operation of the chopper element relative to the radiation pulse, and the positioning of the camera lens, a formula may be applied to the chopper element of FIG. 6. Given the following parameters:

R-inner chopper disc radius,
r-diaphragm radius of camera indicated at 192 in FIG. 6,
n-number of blades,
v-chopper's speed of rotation,
$T_c$-time between positions 184 and 190 when the diaphragm is completely covered,
$T_o$-time between positions 190 and 188 when the diaphragm is completely uncovered,
$T_{op}$-time between positions when leading edge 184 crosses from one side to the other of the diaphragm 192, From the geometry of this system one can develop the following formulae:

$$T_c = T_o \cong \frac{\pi R/n - 2r}{2\pi(R-r)v} \text{ and } T_{op} \cong \frac{r}{(R-r)v\pi}$$

As an example where R=65 mm, r=10 mm, n=2 and v=130 rps, then based on the above formulae:

$$T_c = T_o \cong 1830 \text{ μs and } T_{op} \cong 445 \text{ μs}$$

The flash can be triggered at any moment between positions 126 and 178, the actual delay time when the be in the range of about 300 to 1830 μs depending on relative circumferential positions of the flashlamp and the diaphragm.

Similarly for the flashlamp opening 202 at the radius f and for outer chopper disc radius L, the time $T_{opf}$, which is between positions when trailing edge 176 crosses from one side to the other of the flashlamp opening 202, is:

$$T_{opf} = \frac{f}{(L-f)V \cdot \pi}$$

for f=10 mm, L=95 mm, V=130 r.p.s.

$T_{opf} \cong 290$ μsec

The same type of formulae can be used, of course, to calculate the time relations for the previously described two chopper system.

The apparatus of FIG. 4 can therefore accomplish the same function as the apparatus of FIG. 1, although in a more compact system. As discussed with respect to FIG. 1, the apparatus of FIG. 4 must operate in a dark room or be housed in a cabinet generally indicated by outline 194. The cabinet is equipped with a suitable hatch or lid to permit replacement of the sample in the container 128, and replacement of the photographic film in camera 132.

It is understood that the fluorophore used in the diagnostic methodology has the characteristics to fluoresce on a repetitive basis when repetitively excited, hence the apparatus may be operated over a desired time interval, for example, anywhere from few seconds to one half hour or more, to repetitively expose the photographic film to any fluorescent radiation which may be present after the background fluorescent radiation has subsided. This is particularly useful when it is expected that the concentration of the fluorophore in the sample being analyzed is very low, which may often be the case when analyzing for DNA segments. Hence, over a period of time sufficient photon energy from the fluorescing fluorophore sufficiently exposes the photographic film in the camera to indicate its presence. To assist in such microanalysis, the photographic film in the camera is obviously of high speed characteristic, having a speed rating in excess of 1,000 ASA. Furthermore, to increase the sensitivity of the film, it may be sensitized by partially exposing the photographic film before use in the camera 132. It is also appreciated that an image intensifier may be used to collect photons of fluorescent radiation, amplify the incoming count of photons and then actuate a light emitting device at the amplified signal level to expose the photographic film.

The flashlamp as used in the system may be Xenon type flashlamp or a laser, or any other pulsed source of UV radiation. A continuous wave source could be applied also on the assumption that its pulsation is fully accomplished by a mechanical chopper located in its front, although it could result in wasting lamp output energy. The system is particularly useful in probing for oligonucleotide segments such as DNA or messenger RNA.

The average wattage or power of the lamp producing the excitation energy may be in the range of 60 watts which is, in our case, sufficient to produce the necessary excitation in the fluorophores if present in the sample. An additional factor which impacts on the amount of necessary power of the radiation is the extent to which the incident beam is focused on the sample. According to a preferred embodiment of this invention the lens system focuses the incident radiation into the shape of a circular spot having a diameter approximately from 1 cm to 10 cm, depending on sample size and strength of its fluorescence.

According to this invention an apparatus is provided of relatively inexpensive component construction which provides for the measurement of very low concentrations of fluorophores, usually associated with DNA probing techniques or other very sensitive diagnostic techniques such as immunoassays.

The following examples demonstrate particular features of the invention in analyzing for the presence of various DNA sequences.

EXAMPLE 1

An 0.01 mM stock solution of 4,7-bis(sulphophenyl)-1,10-phenanthroline-2,9-dicarboxylic acid sodium salt (hydrolyzed BCPDA sodium salt, solution A) was prepared in 50 mM 1,3-bis[tris(hydroxymethyl)-methylamino]propane (BTP) buffer, pH=8.0. A 1.0 mM stock solution of europium(III) chloride in 1 M hydrochloric acid (solution B) was also made. Solutions containing 10 nM BCPDA and 100 nM $Eu^{3+}$, 1 nM BCPDA and 100 nM $Eu^{3+}$, 100 pM BCPDA and 100 nM $Eu^{3+}$ and 10 pM BCPDA and 100 nM $Eu^{3+}$ were prepared by diluting necessary aliquots of solutions A and B in 50 nM BTP buffer, pH=6.6. 1.0 μL aliquots of these solutions were deposited on a nylon DNA hybridization membrane (Biorad, Zeta Probe, 50×50 mm) and air dried to form fluorescent spots ca. 3 mm in diameter. These spots contained 10 fmol, 1.0 fmol, 100 amol, and 10 amol of the BCPDA-$Eu^{3+}$fluorescent chelate, respectively. The membrane was mounted on the apparatus of FIG. 2 with a 60 W average power xenon type flashlamp (EG&G) with frequency of pulsation of 200 Hz and a two chopper system with 2 apertures in both chopper discs. The exposure time was 180 s on a Polaroid TM type 612, 20,000 ASA film. The detection limit of the BCPDA-$Eu^{3+}$fluorescent chelate under these experimental conditions was 100 amol (60 fg) and was clearly distinguished from control spots containing only $Eu^{3+}$in buffer or BCPDA without added $Eu^{3+}$

EXAMPLE 2

An 800 μM stock solution (solution A) of an oligonucleotide conjugate with 4-(chlorosulphonyl)-1,10-phenanthroline-2,9-dicarboxylic acid (Eurofluor S1) (compound 1) of the following formula was prepared in distilled, deionized water. Separately, a stock solution of 1 mM europium(III) chloride in 1 M hydrochloric acid (solution B) was also made. Several solutions containing 80 μM of compound 1 and 10 μM $Eu^{3+}$, 8 μM of compound 1 and 10 μM $Eu^{3+}$, 800 nM of compound 1 and 10 μM $Eu^{3+}$, and 80 nM of compound 1 and 10 μM $Eu^{3+}$were prepared by diluting necessary aliquots of solution A and B is mM BTP buffer, pH=6.6. 0.5 μL aliquots of these solutions were deposited on a nylon DNA hybridization membrane (Biorad, Zeta Probe, 50×50 mm) and air dried to form fluorescent spots ca. 3 mm in diameter. These spots contained 40 pmol, 4 pmol, 400 fmol and 40 fmol of 1-$Eu^{3+}$fluorescent chelate, respectively. The membrane was mounted in the apparatus of FIG. 4, with a 60 W average power xenon type flashlamp (EG&G) with frequency of pulsation of 400 Hz and one chopper only in front of the camera lens with 4 apertures in the chopper disc. The exposure time was 80 s on a Polaroid type 612, 20,000 ASA film. The detection limit of the 1-$Eu^{3+}$fluorescent chelate complex under these experimental conditions was 40 fmol (ca. 100 pg) and was clearly distinguished from control spots containing only $Eu^{3+}$or 1 without added $Eu^{3+}$. Similar results have been obtained for a EuroFluor S1-24 mer oligonucleotide conjugate (sequence 5',-CTA TAG TGT CAC CTA AAT CGT ATG).

Compound 1

EXAMPLE 3

An 80 μM stock solution of compound 1 was prepared in distilled water. This solution was further diluted in distilled water to make 80 μM, 8 μM, 80 nM and 80 nM solutions of 1. 0.5 μL aliquots of these solutions were spotted onto acrylamide gel (Pharmacia PhastGel TM, 8 to 25% crosslinked gradient gel) and were electrophoresed in the PhastGel system (280 Vhr at 15°0 C.). The gel was spun in an aqueous solution of 10 μM EuCl$_3$ in 0.1 M tris-(hydroxymethyl)aminomethane buffer, pH 8.0 for 5 min, then washed in distilled water for 2 min and dried over 10 minutes using a hot air dryer. It was then measured in the TRP instrument, using a 60 W average power xenon flashlamp (EG&G) and frequency of pulsation of 400 Hz, and one chopper in front of the camera lens with 4 apertures in the chopper disk. Exposure time was 80 s on a Polaroid type 612, 20,000 ASA film. The detection limit of the fluorescent oligonucleotide in the narrow electrophoretic band was ca. 40 fmol (ca. 0.1 ng)=100 pg and was clearly distinguished from the nonspecific background fluorescence in the gel.

While preferred embodiments have been described and illustrated herein, a person skilled in the art will appreciate that changes and modifications may be made therein without departing from the spirit and scope of this invention as defined in the appended claims.

We claim:

1. An apparatus for time-resolved photographic analysis of an excited sample capable of emitting fluorescent radiation, said apparatus comprising means for emitting radiation pulses at a prescribed frequency for exciting a sample which may contain a label capable of fluorescing on a prolonged basis when excited compared to short-lief background fluorescence of a sample, means for holding a sample to be analyzed, means for focusing radiation pulses emitted by said radiation emitting means along a first path towards a sample held by said holding means, a camera focused along a second path on a sample held by said holding means where said second path diverges in relation to said first path, said camera being adapted to expose continuously a photographic film in said camera at least while said apparatus is in operation, a rotating chopper element having at least one aperture located therein which repetitiously crosses said second path, drive means for rotating said chopper element, means for coordinating phase relationship of the rotation of said chopper element relative to said prescribed frequency of radiation pulses from said emitting means, said coordinating means being adjustable to select a phase relationship which causes each of said apertures to cross said second path to expose photographic film of said camera to fluorescent radiation emitted by a fluorescing label present in a sample after short-life background fluorescence of sample components has subsided and before the next pulse of radiation from said emitting means occurs, said photographic film of said camera being repetitively exposed to fluorescent radiation to record thereby all photon energy from repetitive exposures on said photographic film of fluorescent radiation received from repetitive fluorescent emissions of a fluorescing label in a sample being analyzed.

2. An apparatus of claim 1 wherein said apparatus is housed in a cabinet adapted to provide a total dark space within during operation of said apparatus.

3. An apparatus of claim 1 wherein said chopper element has diametrically aligned first and second apertures, each said aperture extending in a circumferential direction, said first and second apertures having radially extending leading and trailing edges as determined by direction of rotation of said chopper element, means for detecting said leading edge of said first or second aperture to indicate thereby that the leading edge of the other of said first or second apertures is about to enter said second path and commence exposure of photographic film to fluorescent radiation emitted by a fluorescing label in a sample, said detecting means having means for generating and transmitting a signal to said coordinating means to indicate position of said first aperture leading edge relative to said second path, said coordinating means in response to said signal timing out a delay period before actuating said emitting means to emit the next pulse of radiation to ensure that said leading edge of said second aperture crosses said second path after short life background fluorescence of sample components has subsided.

4. An apparatus of claim 1 wherein a second rotating chopper has at least one aperture located therein which repetitively crosses said first path, second drive means for rotating said second chopper element, said coordinating means controlling rotation of said second rotating chopper to transmit through said aperture pulsed radiation from said emitting means of a selected duration.

5. An apparatus of claim 4 wherein first and second rotating choppers are combined in a single rotating chopper element, said at least one aperture passing through said first path being at a first radial location on said element and said at least one aperture passing through said second path being at a second radial location on said element, said second radial location being spaced from said first radial location, said at least one aperture at said first radial location being offset circumferentially relative to said at least one aperture at said second radial location to pass thereby pulsed radiation of a desired duration and to pass fluorescent radiation from a fluorescent label in a sample after background fluorescent radiation has subsided.

6. An apparatus of claim 5 wherein said emitting means is offset from said camera, said first path from said emitting means extending parallel to said second path, means for reflecting at an angle pulsed radiation from said emitting means towards a sample in said holder.

7. An apparatus of claim 6 wherein said first radial location is positioned radially outwardly of said second radial location, each of said apertures having leading and trailing radially extending edges relative to the direction of rotation, said trailing edge of said aperture in said first radial location being spaced from said leading edge of an adjacent said aperture a predetermined number of degrees to chop radiation travelling along said first and second paths in said phase relationship as determined by said coordinating means.

8. An apparatus of claim 1 wherein said emitting means is a flashlamp, a laser or a continuous wavelamp.

9. An apparatus of claim 1 wherein said camera is loaded with a high speed photographic film.

10. An apparatus of claim 1 wherein said camera is loaded with a sensitized photographic film.

11. An apparatus of claim 8 wherein said flashlamp or laser emits a pulse of UV radiation having a pulse width of less than 500 $\mu$s.

12. An apparatus of claim 9 wherein photographic film in said camera is exposed repetitively to fluorescent radiation if present for approximately 2000 $\mu$s.

* * * * *